United States Patent
Saito et al.

(10) Patent No.: US 7,604,352 B2
(45) Date of Patent: Oct. 20, 2009

(54) INSTRUMENT FOR MEASURING A REFRACTIVE POWER

(75) Inventors: Nobuo Saito, Tokyo (JP); Yasuhide Takahashi, Tokyo (JP); Kenichi Takahashi, Tokyo (JP); Yuuichi Kimura, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 0 days.

(21) Appl. No.: 12/157,336

(22) Filed: Jun. 10, 2008

(65) Prior Publication Data

US 2008/0309875 A1 Dec. 18, 2008

(30) Foreign Application Priority Data

Jun. 12, 2007 (JP) .............................. 2007-155226

(51) Int. Cl.
*A61B 3/10* (2006.01)
*A61B 3/14* (2006.01)

(52) U.S. Cl. ........................................ 351/211; 351/208
(58) Field of Classification Search .......... 351/200–246
See application file for complete search history.

(56) References Cited

U.S. PATENT DOCUMENTS

| | | | |
|---|---|---|---|
| 4,526,451 A | * | 7/1985 | Nohda ........................ 351/211 |
| 5,428,414 A | | 6/1995 | Iwane |
| 5,561,482 A | * | 10/1996 | Miyake ...................... 351/208 |
| 5,612,754 A | | 3/1997 | Tanaka |

FOREIGN PATENT DOCUMENTS

| | | |
|---|---|---|
| JP | 6-165757 | 6/1994 |
| JP | 7-213485 | 8/1995 |
| JP | 8-191795 | 7/1996 |

* cited by examiner

*Primary Examiner*—Mohammed Hasan
(74) *Attorney, Agent, or Firm*—Dilworth & Barrese LLP (57) ABSTRACT

An instrument for measuring a refractive power includes a target, a target projecting unit, a measurement light projecting unit, a light receiving unit, a unit for performing a normal refractive power measurement, a judgment unit, and a unit for performing a high-speed refractive power measurement. The unit for performing a normal refractive power measurement measures a normal refractive power of an examined eye based on received light data. The judgment unit judges reliability of the received light data or the refractive power measurement. The unit for performing a high-speed refractive power measurement measures a refractive power of the examined eye faster than the unit for performing a normal refractive power measurement in response to a judgment result of the judgment unit.

5 Claims, 5 Drawing Sheets

INSTRUMENT FOR MEASURING A REFRACTIVE POWER

This application is based on and claims the benefit of priority from Japanese Patent Application No. 2007-155226, filed on 12 Jun. 2007, the content of which is incorporated herein by reference.

BACKGROUND OF THE INVENTION

1. Field of the Invention

The present invention relates to an instrument for measuring a refractive power of an examined eye.

2. Related Art

Conventionally, an instrument for measuring a refractive power has been widely used in various medical fields including departments of opthamology. For example, an instrument utilizing retinoscopy is described in Japanese Unexamined Patent Application Publication No. H06-165757.

The above instrument includes a handheld type that is used for a case where measurement with a stand alone type set on a table is difficult, such as measurements for babies, children, people in wheelchairs, or the like (Japanese Unexamined Patent Application Publication No. H07-213485).

However, when measurements are performed for babies, children, people in wheelchairs, and the like using the handheld type instrument, it is sometimes impossible to acquire sufficient measurement data due to handshaking of an operator and an insufficient time period during which babies and children can keep the eye motionless.

Even if the stand alone type instrument is used, unstable measurement data may be acquired in some cases: when a measurement is performed for a person who has a small pupil, or an abnormal eye position in addition to babies and children, for example. Unstable measurement data may result in problems such as requiring a long time period before obtaining a measurement value and failure to obtain the measurement value.

As a method of performing a refractive power measurement in the above cases, Japanese Unexamined Patent Application Publication No. H08-191795 discloses a method in which an operator operates a switch to change the number of data acquisition.

However, the method of Japanese Unexamined Patent Application Publication No. H08-191795 involves a cumbersome operation of the switch.

Also, the method forces an examinee to have repeated measurements, causing difficulty in measuring the eyes of babies and children.

SUMMARY OF THE INVENTION

The present invention is directed to provide an instrument capable of measuring a refractive power within a short time period, without necessitating a cumbersome operation.

The present invention resolves the above described problems by the following means.

In an aspect of the present invention, an instrument for measuring a refractive power of an examined eye is provided, which include a target, a target projecting unit, a measurement light projecting unit, a light receiving unit, a unit for performing a normal refractive power measurement, a judgment unit, and a unit for performing a high-speed refractive power measurement. The target is movable in an optical axis direction of the examined eye. The target projecting unit projects the target onto the examined eye. The measurement light projecting unit intermittently projects light into a pupil of the examined eye. The light receiving unit receives measurement light that is projected by the measurement light projecting unit and reflected from the examined eye while the target is at rest. The light receiving unit also outputs received light data corresponding to the measurement light. The unit for performing a normal refractive power measurement measures a normal refractive power of the examined eye based on the received light data. The judgment unit judges reliability of the received light data or the refractive power measurement. The unit for performing a high-speed refractive power measurement measures a refractive power of the examined eye faster than the unit for performing a normal refractive power measurement in response to a judgment result of the judgment unit.

With the instrument for measuring a refractive power described above, it is possible to measure the refractive power within a short time period without necessitating cumbersome operations.

In another aspect of the present invention, an instrument for measuring a refractive power is provided, in which the unit for performing a normal refractive power measurement performs one refractive power measurement using a plurality of sets of received light data and the judgment unit judges the reliability of the received light data based on distribution of the plurality of sets of received light data.

In the instrument for measuring a refractive power described above, the judgment unit can provide a highly accurate judgment since the judgment unit judges the reliability of the received light data based on the distribution of the plurality of sets of received light data, judging the reliability based on the data variance.

In still another aspect of the present invention, an instrument for measuring a refractive power is provided, in which the judgment unit judges the reliability of the data based on elapsed time from a start of acquisition of the received light data.

In the instrument for measuring a refractive power described above, the judgment unit can perform a quick judgment without repeating the measurement until data is acquired, since the judgment unit judges the reliability of the data based on the elapsed time from the start of acquisition of received light data. Therefore, the measurement of the refractive power can be achieved within a short time period.

In yet another aspect of the present invention, an instrument for measuring a refractive power is provided, in which the unit for performing a normal refractive power measurement performs one refractive power measurement using a plurality of sets of received light data; and the unit for performing a high-speed refractive power measurement performs one refractive power measurement using fewer sets of received light data than the unit for performing a normal refractive power measurement.

In the instrument for measuring a refractive power described above, the unit for performing a high-speed refractive power measurement can measure a refractive power with a simple configuration within a short time period, since this unit performs the measurement of the refractive power of the examined eye using fewer sets of received light data than those used in one refractive power measurement by the unit for performing a normal refractive power measurement.

In a further aspect of the present invention, an instrument for measuring a refractive power is provided, in which the unit for performing a high-speed refractive power measurement shortens a time interval of light projection into the pupil of the examined eye performed by the measurement light projecting unit.

In the instrument for measuring a refractive power described above, the unit for performing a high-speed refractive power measurement can measure a refractive power using a plurality of sets of received light data within a short time period, since the measurement light projecting unit shortens the time interval for intermittently projecting light into the pupil of the examined eye.

BRIEF DESCRIPTION OF THE DRAWINGS

FIG. 2 illustrates a pattern of a chopper 61a;

DETAILED DESCRIPTION OF THE INVENTION

Without necessitating cumbersome operations, the present invention accomplishes a purpose of providing a instrument capable of measuring a refractive power within a short time period, by having the judgment unit for judging the reliability of the measurement and the high-speed refractive power measurement unit for performing the measurement of the refractive power of the examined eye faster than the normal refractive power measurement unit in response to the judgment result of the judgment unit.

Figure 1:
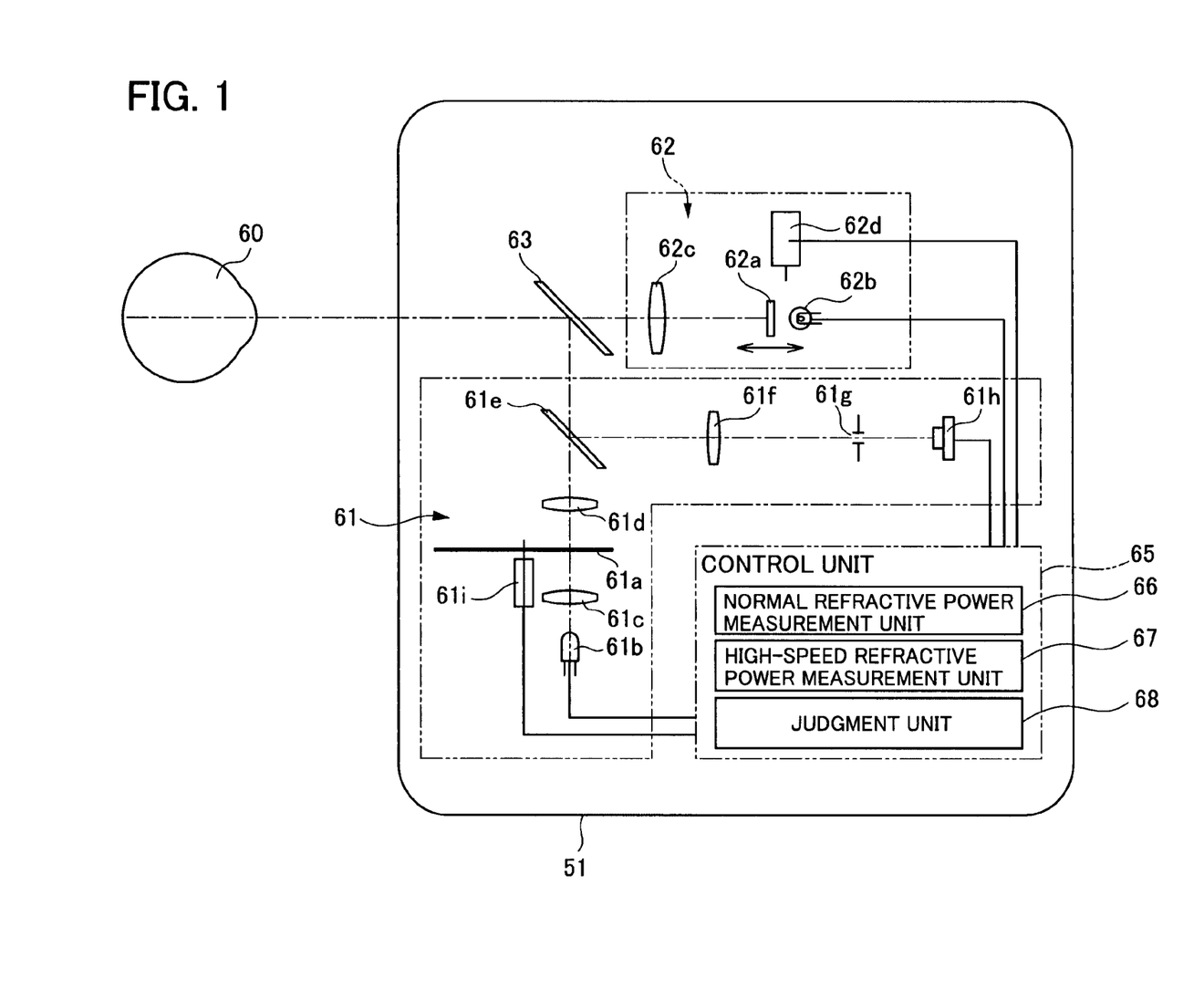
FIG. 1 illustrates an exemplary embodiment of an instrument for measuring a refractive power.

Each of the drawings including FIG. 1 illustrates a diagram of the instrument in which size and shape of each part are exaggerated as appropriate for purposes of illustration in order to facilitate the understanding of the present invention.

Further, in the following description, specific values, shapes, and the like are used for purposes of description, which, however, can be changed as required.

An instrument 51 for measuring a refractive power is of a handheld type which includes a measurement unit 61, a projection unit 62, a dichroic mirror 63, a control unit 65, and the like, and which can perform a measurement while an operator holds the instrument by hands.

The projection unit 62 is a unit to project a target, including a convex lens 62c, a target 62a, and a visible light source 62b, arranged in this order closer to an examined eye 60, and further including a motor 62d.

Rays of light from the target 62a illuminated by the visible light source 62b are transformed to a substantially parallel light beam through the convex lens 62c, entering the examined eye 60. Therefore, the examined eye 60 sees a position of the target 62a as if it lies more remotely than it actually does.

In the projection unit 62, the target 62a and the visible light source 62b are movable in an optical axis direction (a direction indicated by an arrow in FIG. 1), being driven by the motor 62d via a target movement mechanism (not shown). At this time, the target 62a and the visible light source 62b move in the optical axis direction of the examined eye 60 while the relative position between them is maintained constant.

The measurement unit 61 measures a refractive power by detecting a moving speed of a shadow on a pupil using a measurement principle of retinoscopy.

The measurement unit 61 includes a measurement light projecting portion, a light receiving unit 61h, a half mirror 61e, a lens 61f, and an aperture diaphragm 61g. The measurement light projecting unit includes a chopper 61a having a slit, a motor 61i for rotating the chopper 61a, an infrared light source 61b for illuminating the chopper 61a, a lens 61c, and a lens 61d for projecting a pattern formed by the chopper 61a onto an eye ground of the examined eye 60. The light receiving unit 61h detects a moving speed of the pattern formed by light reflected from the eye ground of the examined eye 60.

The dichroic mirror 63 introduces the measurement light (infrared light) emitted from the measurement unit 61 and the measurement light (visible light) emitted from the projection unit 62 into the examined eye 60, respectively, and returns the infrared light reflected from the examined eye 60 to the measurement unit 61. Since the chopper 61a rotates, the pattern to be projected onto the eye ground of the examined eye 60 moves, intermittently projecting light into the pupil. The moving speed of the pattern formed on the light receiving unit 61h varies according to the refractive power of the examined eye 60.

Figure 2:
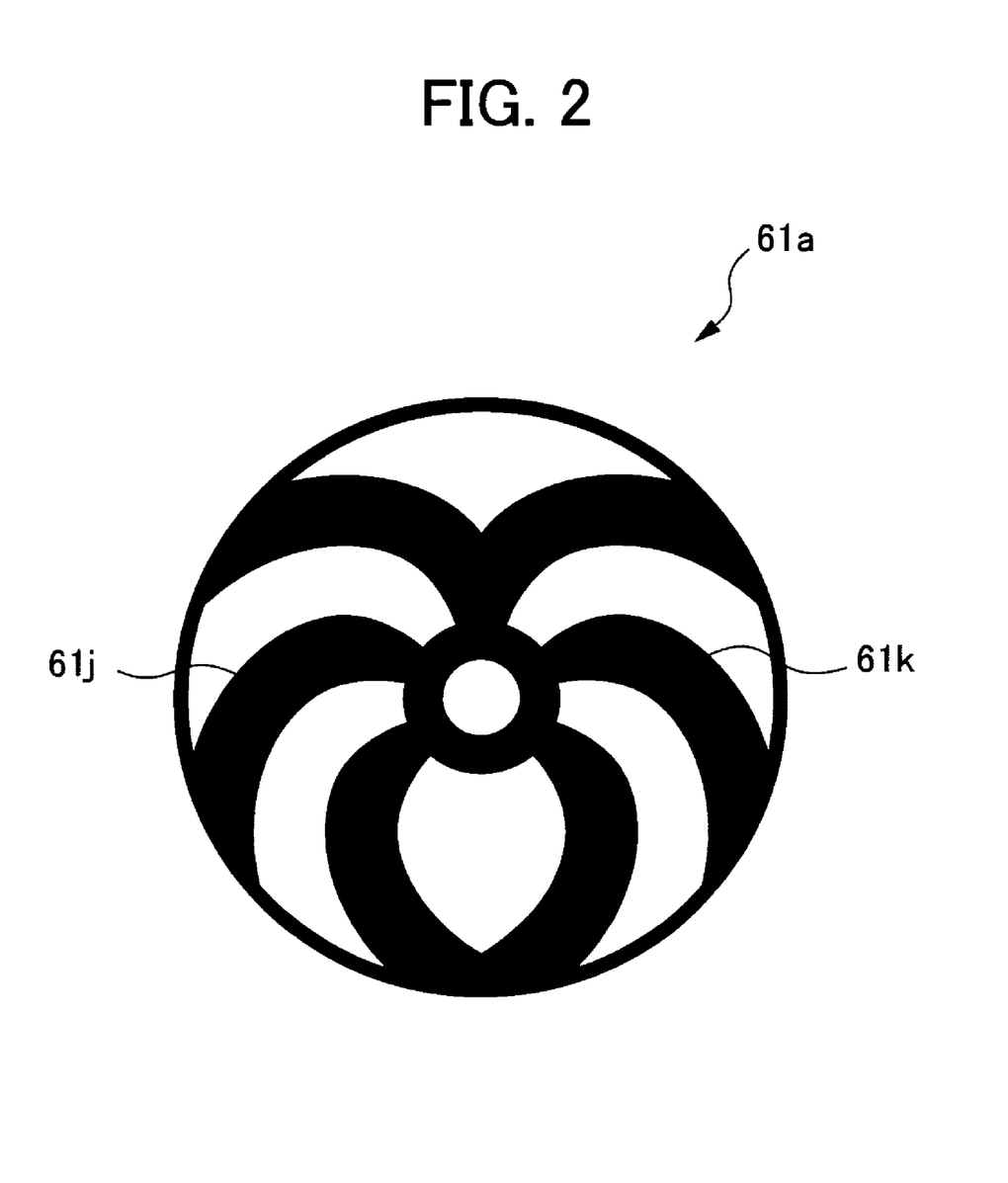

FIG. 2 illustrates the pattern of the chopper 61a.

As shown in FIG. 2, patterns 61j and 61k extending in two directions are formed on the chopper 61a. An image of the pattern is reflected from the pupil of the examined eye 60 to form on the light receiving unit 61h after one rotation of the chopper 61a. The light receiving unit 61h uses an image sensor capable of capturing the reflected light from the pupil of the examined eye 60. The image sensor defines two pairs of light receiving regions in signal processing, which lie in a direction of scanning the patterns 61j and 61k for the examined eye 60. A phase difference of the output signals of the paired light receptive regions (hereinafter referred to as "phase difference data") is measured so as to produce a direction of motion and a size of the light pattern, with which a refractive power such as a spherical power, an astigmatic degree, and an astigmatic axis is calculated. The phase difference data output by the light receiving unit 61h, which is converted by an A/D converter (not shown) from an analog signal to a digital signal, is sent to the control unit 65. In the present embodiment, a set of phase difference data can be acquired from the light receiving unit 61h for each rotation of the motor 61i (one rotation of the chopper 61a).

Returning to FIG. 1, the control unit 65 includes a Central Processing Unit (CPU), a circuit with a memory for an operation of the CPU and the like. Referring to the phase difference data output from the light receiving unit 61h, the control unit 65 performs control and calculation for the visible light source 62b, the infrared light source 61b, and the motors 62d and 61i. The control unit 65, while driving the measurement unit 61, refers to output thereof. The control unit 65 also controls the motor 62d while driving the visible light source 62b, performing positioning of the target 62a and the visible light source 62b and a scanning of the positions thereof.

Also, the control unit 65 includes a normal refractive power measurement unit 66, a high-speed refractive power measurement unit 67, and a judgment unit 68. The normal refractive power measurement unit 66, the high-speed refractive power measurement unit 67, and the judgment unit 68 perform measurement of a refractive power, such as a spherical power, an astigmatic degree, and an astigmatic axis, while they control the measurement unit 61 and the projection unit 62.

The normal refractive power measurement unit 66 obtains phase difference data 7 times for one measurement of a refractive index of an eye, and ranks the seven sets of phase difference data in order of size. The unit 66 calculates a refractive power such as a spherical power, an astigmatic degree, and an astigmatic axis by using the fourth phase difference data (namely, a median). Various types of statistical processing, such as using an average value or the like, may be performed, instead of using the median.

Figure 3:
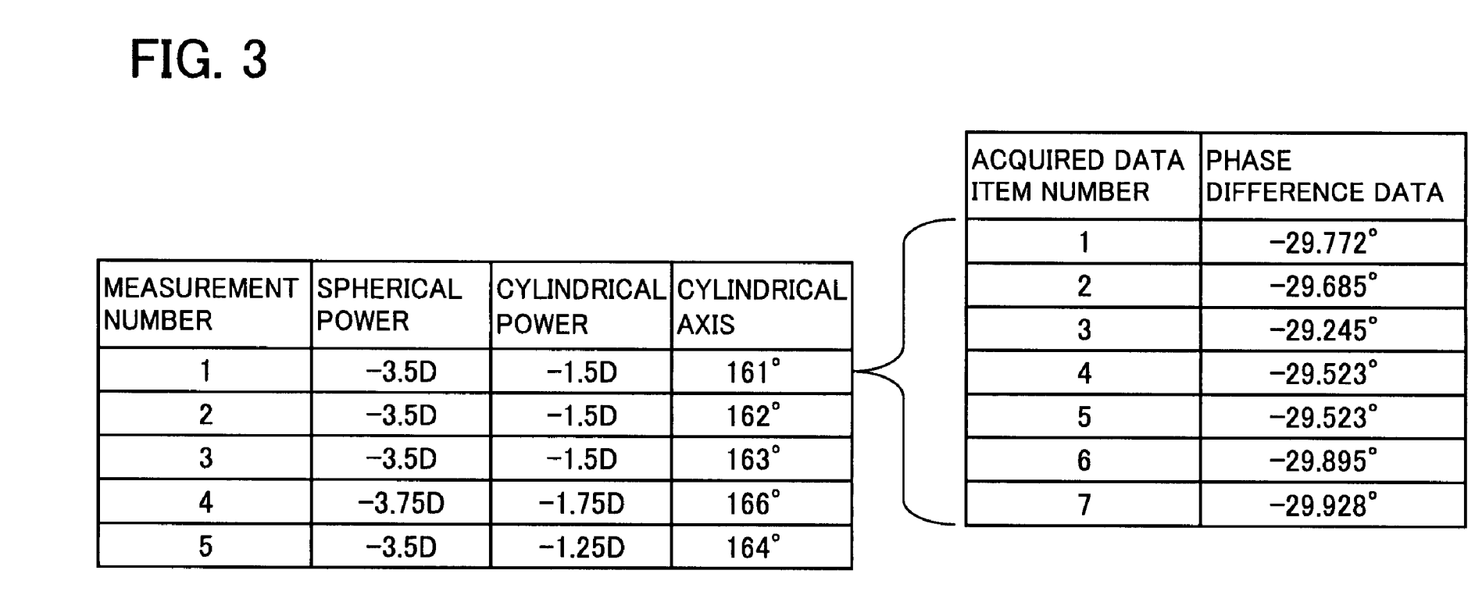
FIG. 3 illustrates data handling during measurement performed by a normal refractive power measurement unit.

FIG. 3 illustrates how the data is processed when the normal refractive power measurement unit 66 performs a measurement.

In FIG. 3, a spherical power and an astigmatic degree are represented by "Diopter" as a unit, and an astigmatic axis and phase difference data are represented by "degree" as a unit.

In the instrument 51 for measuring a refractive power according to the present embodiment, the number of measurements can be selected as appropriate, and FIG. 3 exemplifies a case where five measurements are performed. In each of the five measurements, the normal refractive power measurement unit 66 acquires seven sets of phase difference data to calculate a refractive power.

Returning to FIG. 1, the high-speed refractive power measurement unit 67 acquires phase difference data three items in one measurement of refractive index of an eye, and ranks the three sets of phase difference data in order of size. The unit 67 calculates a refractive power such as a spherical power, an astigmatic degree, and an astigmatic axis by using the second phase difference data (namely, a median). Various types of statistical processing, such as using an average value or the like, may be performed instead of using the median.

The sets of acquired phase difference data differ between the normal refractive power measurement unit 66 and the high speed refractive power measurement unit 67. Since the unit 66 acquires more sets of phase difference data than the unit 67, the unit 66 provides better reliability for the refractive power obtained. On the other hand, since the high-speed refractive power measurement unit 67 acquires fewer sets of phase difference data than the normal refractive power measurement unit 66, the unit 67 can acquire the necessary data at higher speed compared to the unit 66.

Therefore, a measurement by the normal refractive power measurement unit 66 is suitable for cases where the measurement is performed under stable conditions, for example, cases where an examinee is an adult and not suffering from an eye disease. On the other hand, the measurement by the high-speed refractive power measurement unit 67 is suitable for cases where a measurement is performed for an examinee who has difficulty in keeping his eyes still during measurement, such as babies and infants, cases where a measurement is performed for an examinee in an unstable position, and cases where an examinee is suffering from a small pupil, an abnormal eye position, or other diseases. Since the measurement by the high-speed refractive power measurement unit 67 has lower reliability for the refractive power than that of the normal power measurement unit 66 as described above, it is preferable to perform the measurement using the unit 66 as much as possible.

In the present embodiment, as described above, since the only difference between the normal refractive power measurement unit 66 and the high speed refractive power measurement unit 67 is the sets of acquired phase difference data, there are not two units separated with each other as hardware, but the functions of the units 66 and 67 are implemented by software.

Hereinafter, a measurement operation of the refractive power by the normal refractive power measurement unit 66 is referred to as a normal measurement mode, whereas a measurement operation of the refractive power by the high speed refractive power measurement unit 67 is referred to as a high-speed measurement mode.

The judgment unit 68 judges reliability of measurement of the phase difference data based on distribution of the phase difference data acquired by the normal refractive power measurement unit 66. Operation of the judgment unit 68 will be described sequentially in the following description of the measurement operation of the instrument 51 for measuring a refractive power.

Figure 4:
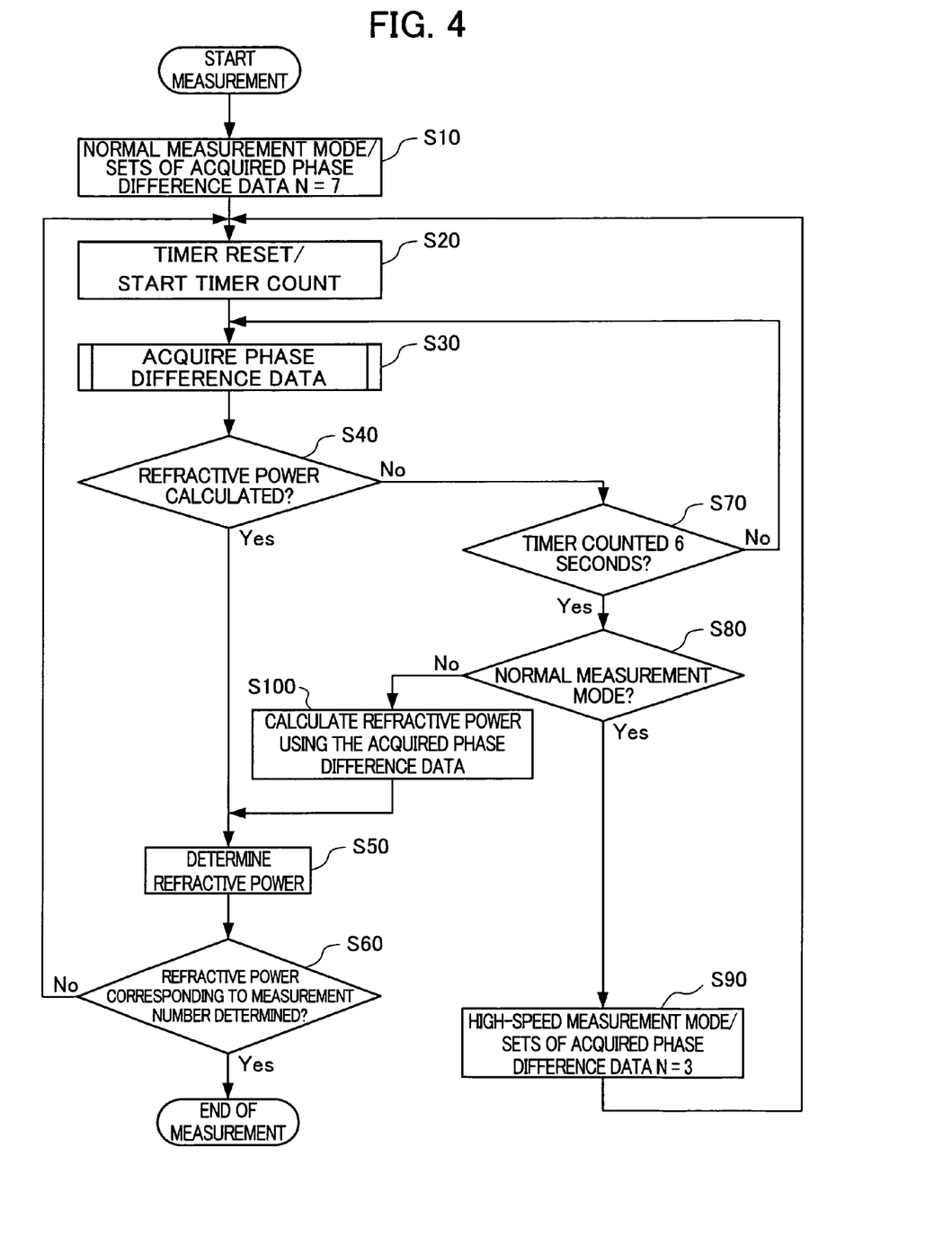
FIG. 4 is a flow chart illustrating operation of the instrument for measuring a refractive power during a measurement.

FIG. 4 is a flow chart illustrating operation of the instrument 51 during a measurement of a refractive power.

When a measurement is started by operating a measurement start switch (not shown), the control unit 65 starts a measurement operation in a normal measurement mode with the normal refractive power measurement unit 66 in step (hereinafter abbreviated by "S") 10 to set N=7 as a parameter representing sets of acquired phase difference data, and advances the processing to S20.

In S20, the control unit 65 resets a timer to start counting, and advances the processing to S30. The above described timer is a clock unit for measuring elapsed time from a start of the acquisition of the phase difference data in the following steps.

In S30, the control unit 65 acquires the phase difference data.

Figure 5:
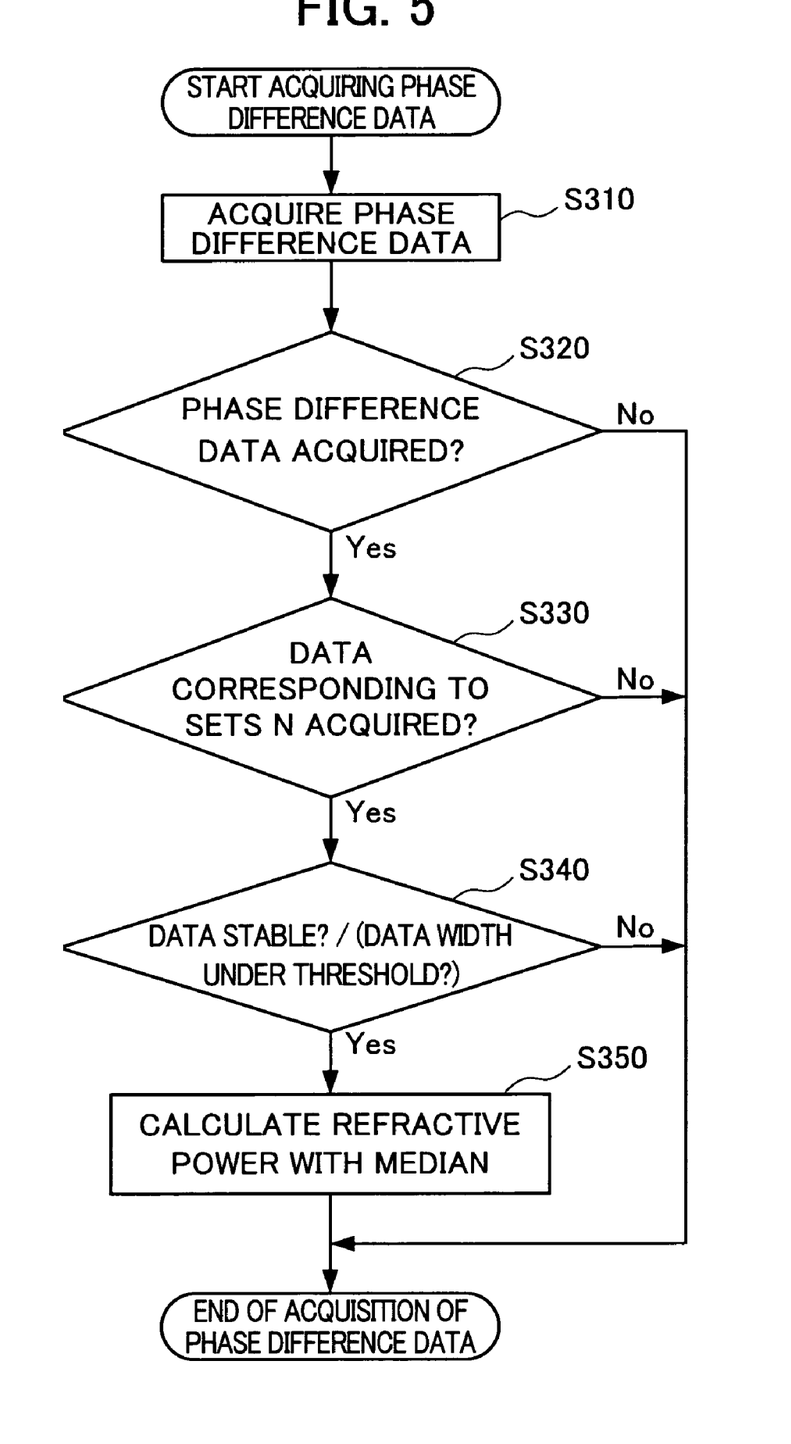
FIG. 5 is a flow chart illustrating in detail a step of acquiring phase difference data in S30 of FIG. 4.

FIG. 5 is a flow chart illustrating details of S30 of FIG. 4.

In S310, the control unit 65 instructs the light receiving unit 61h to acquire the phase difference data in accordance with the number of times set in the parameter N representing the sets of acquired phase difference data. According to the instruction, the light receiving unit 61h acquires the N sets of phase difference data. The light receiving unit 61h outputs the acquired phase difference data to the control unit 65. In the present step, the light receiving unit 61h automatically outputs the acquired phase difference data regardless of the quality of the data.

In S320, the judgment unit 68 judges whether the phase difference data has been acquired. What is judged in the present step is not whether the phase difference data is valid, but whether any phase difference data has been successfully sent from the light receiving unit 61h. If the phase difference data has been acquired, flow proceeds to S330. If the phase difference data has not been acquired, the flow of FIG. 5 is terminated, and flow proceeds to S40 of FIG. 4.

In S330, the judgment unit 68 judges whether N sets of phase difference data have been acquired. If N sets of phase difference data have been acquired, flow proceeds to S340. If N sets of phase difference data have not been acquired, the flow of FIG. 5 is terminated, and flow proceeds to S40 of FIG. 4.

In S340, the judgment unit 68 judges whether the N sets of phase difference data are stable. More specifically, the judgment unit 68 extracts the maximum value and the minimum value from the acquired N sets of phase difference data, and judges the stability according to whether a difference of these values (width of the phase difference data) is under a predetermined threshold. The reason for adopting this method of judgment is that the width of the phase difference data can be considered as a value representing a distribution of the phase difference data. If the width of the phase difference data is narrow (if the difference is small), the judgment unit 68 judges that the data has a high reliability since a small variant of the data is considered to show a stable measurement. On the other hand, if the width of the phase difference data is large (if the difference is great), the judgment unit 68 judges that the data has a low reliability since a large variation in the data is considered to show an unstable measurement.

If the data width is under the predetermined threshold, flow proceeds to S350. If the data width exceeds the predetermined threshold, the flow of FIG. 5 is terminated, and flow proceeds to S40 of FIG. 4.

In S350, the control unit 65 ranks the N sets of acquired phase difference data in order of size and selects a median as the data to be used in calculating a refractive power, calculating the refractive power, such as a spherical power, an astigmatic degree, an astigmatic axis, and the like.

Now flow advances to S40 in FIG. 4. The judgment unit 68 judges in S40 whether the refractive power has been calculated in the immediately previous step S30. If the refractive power has been calculated, flow proceeds to S50. If the refractive power has not been calculated, flow proceeds to S70.

In S50, the control unit 65 determines the refractive power (a spherical power, an astigmatic degree, an astigmatic axis), storing it in a memory (not shown).

In S60, the control unit 65 judges whether the refractive power corresponding to the number of measurements has been determined. Here, the number of measurements is 5, for example, as shown in a column "MEASUREMENT NUMBER" of the left table illustrated in FIG. 3, and has no relationship with the number N representing the sets of phase difference data. If the refractive power corresponding to the number of measurements has been determined, the control unit 65 performs a display and outputting of the refractive power (a spherical power, an astigmatic degree, an astigmatic axis) corresponding to the number of measurements, terminating the measurement. The refractive power is displayed and output with the information identifying the measurement mode, normal or high-speed measurement mode. If the refractive power corresponding to the number of measurements has not been determined, the control unit 65 returns the processing to S20 to repeat the measurement.

In S70, the judgment unit 68 judges whether the timer has counted 6 seconds. If the timer has not counted 6 seconds, the control unit 65 returns the processing to S30 to repeat the acquisition of the phase difference data. On the other hand, if the timer has counted 6 seconds, flow proceeds to S80. In the present embodiment, if the measurement is performed under suitable conditions, one measurement of the refractive power can be completed in less than 0.2 seconds. If the measurement takes 6 seconds or more, the control unit 65 judges that the reliability of a measurement is low due to instability in the measurement. It should be noted that the threshold of 6 seconds may be changed as the case may be.

In S80, the control unit 65 judges whether the current measurement is in a normal measurement mode. If the current measurement is in a normal measurement mode, the control unit 65 advances the processing to S90. If it is not, but is in a high-speed measurement mode, the control unit 65 advances the processing to S100.

In S90, the control unit 65 causes the high-speed refractive power measurement unit 67 to start a measurement in a high-speed measurement mode, sets N=3 as a parameter indicating the sets of acquisition of phase difference data, and proceeds to S20.

In S100, the control unit 65 calculates a refractive power using the acquired phase difference data. If flow has been proceeded to S100, it indicates that phase difference data having a high reliability has not been acquired yet, even after the operation has been shifted to a high-speed measurement mode. However, since some phase difference data is usually acquired, the control unit 65 calculates a refractive power with the phase difference data already acquired. In the present embodiment, the control unit 65 calculates a refractive power with an average value of the acquired phase difference data. Since the refractive power obtained in this step, however, has a low reliability, the control unit 65 gives notice of the data quality. If no phase difference data has been acquired although flow has proceeded to this step, the control unit 65 displays an alert, terminating measurement processing.

According to the present embodiment as described above, the instrument for measuring a refractive power performs a measurement in a normal measurement mode immediately after a start of the measurement, acquiring a highly accurate refractive power. If the reliability of the acquired phase difference data is low because of some causes, the instrument switches the operation from a normal to a high-speed measurement mode. Accordingly, since the instrument for measuring a refractive power automatically switches the operation to the high speed measurement mode without a cumbersome switching operation by an operator, the instrument can implement a faster measurement. In this way, the instrument for measuring a refractive power according to the present invention can increase the probability to measure a refractive power in one measurement even for a case where an operator has difficulty in performing a measurement with a conventional instrument. In addition, a highly accurate refractive power can be normally acquired, without a special switching operation.

MODIFIED EMBODIMENT

The present invention is not limited to the above described embodiment, but can be modified and changed into various forms, which are also encompassed within the present invention.

In the embodiment described above, an example has been described in which the judgment unit 68 extracts the maximum value and the minimum value from the phase difference data to perform judgment according to whether the difference (data width) is under the predetermined threshold. However, the present invention is not limited to the above example, and the judgment may be performed according to a distribution of the phase difference data by using a statistical method such as deviation, variance, and standard deviation.

In the embodiment described above, an example has been described in which the judgment unit 68 judges the phase difference data acquired from the light receiving unit 61h. However, the present invention is not limited to the above described example. The judgment unit 68 may alternatively perform the judgment using a refractive power (a spherical power, an astigmatic degree, an astigmatic axis) that is calculated with the phase difference data acquired from the light receiving unit 61h.

In the embodiment described above, an example has been described in which the judgment unit 68 judges the phase difference data using the distribution of the phase difference data and the timer lapsed time. However, the present invention is not limited to the above example. Alternatively, the present invention may use either the distribution of the phase difference data or the timer lapsed time.

In the embodiment described above, an example has been described in which the high-speed refractive power measurement unit 67 facilitates a high-speed operation by decreasing the sets of acquisition of phase difference data. However, the present invention is not limited to the above described example, but may facilitate the high-speed operation by faster rotation of the chopper 61a. Here, the rotation speed of the chopper 61a is set as high as possible within a range in which highly reliable received light data can be acquired. If the chopper 61a is further rapidly rotated, the reliability of the received light data may be lowered. Therefore, it may be preferable to set an upper limit for the rotation speed of the chopper 61a taking that into consideration.

In the embodiment described above, an example is described in which the instrument for measuring a refractive power is of a handheld type. However, the present invention is not limited thereto, but the instrument may be of a desktop type.

What is claimed is:

1. An instrument for measuring a refractive power of an examined eye, comprising:
    a target movable in an optical axis direction of the examined eye;
    a target projecting unit for projecting the target onto the examined eye;
    a measurement light projecting unit for intermittently projecting light into a pupil of the examined eye;
    a light receiving unit that receives measurement light, the measurement light being projected by the measurement light projecting unit and reflected from the examined eye while the target is at rest, and the light receiving unit outputting received light data corresponding to the measurement light;
    a unit for performing a normal refractive power measurement of the examined eye based on the received light data;
    a judgment unit for judging reliability of the received light data or the refractive power measurement; and
    a unit for performing a high-speed refractive power measurement of the examined eye faster than the unit for performing a normal refractive power measurement in response to a judgment result of the judgment unit.

2. The instrument according to claim 1, wherein
    the unit for performing a normal refractive power measurement performs one refractive power measurement using a plurality of sets of received light data; and
    the judgment unit judges the reliability of the received light data based on distribution of the plurality of sets of received light data.

3. The instrument according to claim 1, wherein
    the judgment unit judges the reliability of the received light data based on elapsed time from a start of acquisition of the received light data.

4. The instrument according to claim 1, wherein
    the unit for performing a normal refractive power measurement performs one refractive power measurement using a plurality of sets of received light data; and
    the unit for performing a high-speed refractive power measurement performs one refractive power measurement using fewer sets of received light data than the unit for performing a normal refractive power measurement.

5. The instrument according to claim 1, wherein
    the unit for performing a high-speed refractive power measurement shortens a time interval of light projection into the pupil of the examined eye performed by the measurement light projecting unit.

* * * * *